United States Patent

Greene et al.

Patent Number: 5,065,861
Date of Patent: Nov. 19, 1991

[54] TREATED DENTAL FLOSS AND DISPENSER

[76] Inventors: Michael D. Greene, 100 Woodsville Rd., Hopewell, N.J. 08525; George Spector, 233 Broadway Rm 3815, New York, N.Y. 10007

[21] Appl. No.: 582,407

[22] Filed: Sep. 14, 1990

[51] Int. Cl.⁵ .................. A61B 19/02; A61C 15/00
[52] U.S. Cl. .................. 206/63.5; 132/325; 206/210; 206/368; 242/171
[58] Field of Search .............. 206/63.5, 368, 581, 206/438, 210; 242/171; 132/321, 323–325, 329

[56] References Cited

U.S. PATENT DOCUMENTS

| | | | |
|---|---|---|---|
| 678,101 | 7/1901 | Cowan | 242/171 |
| 2,554,526 | 5/1951 | Dembenski | 132/325 |
| 4,019,522 | 4/1977 | Elbreder | 132/325 X |
| 4,034,770 | 7/1977 | Trecker | 206/63.5 X |
| 4,254,786 | 3/1981 | Won | 132/325 |
| 4,660,584 | 4/1987 | Wofford | 132/325 |
| 4,934,389 | 6/1990 | Pettiford | 132/325 |
| 4,941,487 | 7/1990 | VanBeneden | 132/323 |

Primary Examiner—Bryon P. Gehman

[57] ABSTRACT

An improved dental floss dispenser is provided and consists of a roll of waxed dental floss having a shaft that is rotatably supported in a chamber of a container with a quantity of powdered baking soda. Spring biased perforated sandpaper in the bottom of the chamber roughens the dental floss when it is pulled out. The container is agitated so that the baking soda can adhere to the roughened dental floss. A cutter on the container is for removing a piece of the roughened dental floss with the baking soda adhered thereupon so it can be utilized in conjunction with hydrogen peroxide when used in areas between the teeth for the treatment of gingivitis.

4 Claims, 1 Drawing Sheet

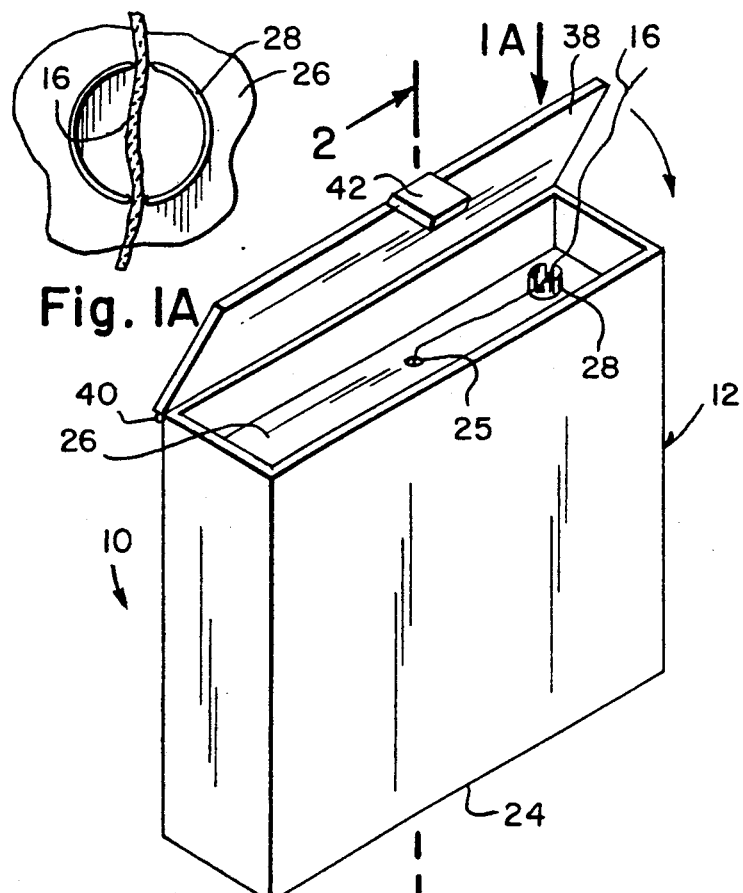
Fig. 1A
Fig. 1
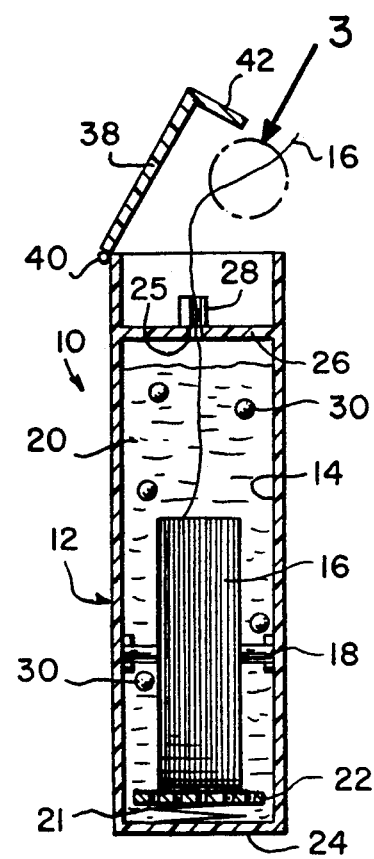
Fig. 2
Fig. 3
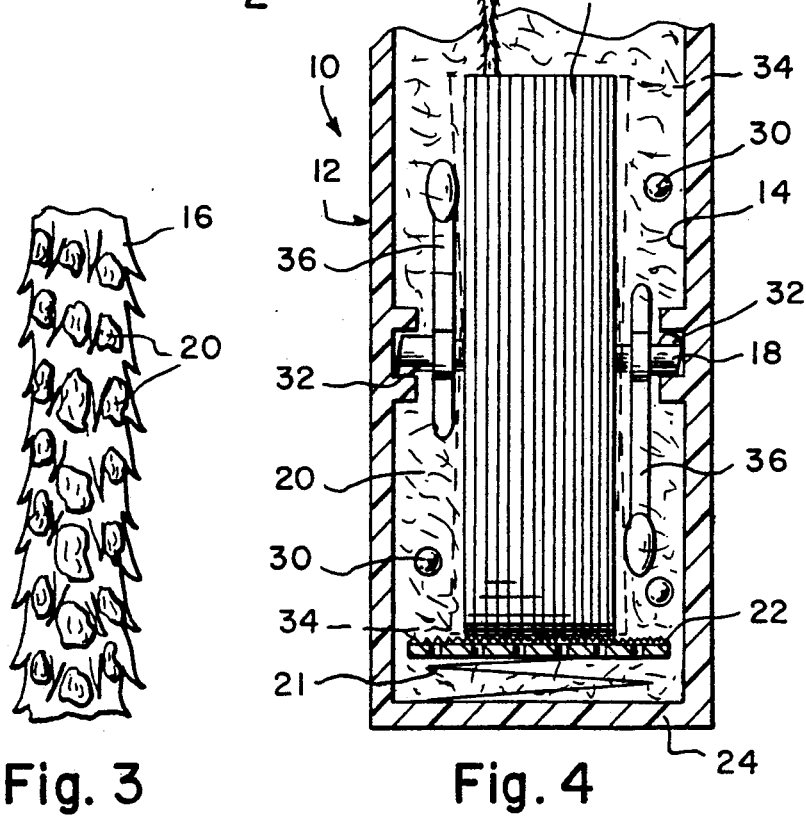
Fig. 4

TREATED DENTAL FLOSS AND DISPENSER

BACKGROUND OF THE INVENTION

The instant invention relates generally to dental floss and more specifically it relates to an improved dental floss dispenser which provides baking soda to the dental floss when being removed from the dispenser.

There are available various conventional dental floss material which do not provide the novel improvements of the invention herein disclosed.

SUMMARY OF THE INVENTION

A primary object of the present invention is to provide an improved dental floss dispenser that will overcome the shortcomings of the prior art devices.

Another object is to provide an improved dental floss dispenser that applies baking soda to roughened dental floss when the dental floss is being removed from the dispenser.

An additional object is to provide an improved dental floss dispenser in which the roughened dental floss with the baking soda thereupon can be utilized in conjunction with hydrogen peroxide when used in areas between the teeth for the treatment of a gum disease called gingivitis.

A further object is to provide an improved dental floss dispenser that is simple and easy to use.

A still further object is to provide an improved dental floss dispenser that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

FIG. 1 is a perspective view of the invention.

FIG. 1A is a top view of the dental floss cutter taken in direction of arrow 1A in FIG. 1.

FIG. 2 is a cross sectional view taken along line 2—2 in FIG. 1, showing the internal structure.

FIG. 3 is an enlarged detail view as indicated by arrow 3 in FIG. 2, showing a piece of the roughened dental floss with the powdered baking soda adhered thereon.

FIG. 4 is an enlarged cross sectional view with parts broken away similar to FIG. 2, showing a modification in which rotation of the roll of dental floss will cause it to wobble while the spoons on the shaft will help stir up the powdered baking soda.

DETAILED DESCRIPTION OF THE PREFERRED EMBODIMENTS

Turning now descriptively to the drawings, in which similar reference characters denote similar elements throughout the several views, FIGS. 1 and 2 illustrate an improved dental floss dispenser 10 consisting of a container 12 having a chamber 14 therein. A roll of waxed dental floss 16 having a shaft 18 is rotatably supported in the chamber 14 of the container 12, while a quantity of powdered baking soda 20 is carried in the chamber 14 of the container 12. An expansion spring 22 is affixed at its lower end to the bottom 24 of the chamber 14 of the container 12. A piece of perforated sandpaper 25 is affixed to the top end of the expansion spring 22 so that the sandpaper 22 will always make contact with the dental floss 16 and rough it up when the dental floss is being pulled out through a hole 25 in a recessed top 26 of the container. If the container 12 is agitated while the roughened dental floss 16 is pulled out, the baking soda 20 will adhere to the roughened dental floss. A cutter 28 on the recessed top 26 of the container 12 (see FIG. 1A) is for removing a piece of the roughened dental floss 16 with particles of the baking soda 20 adhered thereupon as shown in FIG. 3. The dental floss 16 can then be utilized in conjunction with hydrogen peroxide when used in areas between the teeth for the treatment of a gum disease called gingivitis.

A plurality of small balls 30 are provided in the chamber 14 of the container 12 so that when the container is vigorously shaken the small balls 30 will agitate the baking soda 20 to adhere to the roughened dental floss 16.

FIG. 4 shows a modification in which the shaft 18 of the roll of dental floss 16 is rotatably supported in the chamber 14 of the container 12 off center from its axis by oppositely positioned detents 32 on the ends of the shaft 18. When the roll of dental floss 16 rotates it will wobble back and forth, shown in dotted lines 34, to agitate the baking soda 20 to adhere to the roughened dental floss 16. A pair of spoons 36 are affixed transversely in opposite directions onto opposite sides of the shaft 18. When the roll of dental floss 16 rotates, the spoons 36 will turn to also agitate the baking soda 20 to adhere to the roughened dental floss 16.

The container 12 can also have a lid 38 hinged at 40 to one side above the recessed top 26. A latch 42 can keep the lid 38 closed to protect the cutter 28. The container 12 is fabricated out of a durable plastic material, but other types of material can be used, such as metal, cardboard, wood, etc.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. An improved dental floss dispenser comprising:
   a) a container having a chamber therein;
   b) a roll of waxed dental floss having a shaft that is rotatably supported in the chamber of said container;
   c) a quantity of powdered baking soda carried in the chamber of said container;
   d) means in the bottom of the chamber of said container for roughening said dental floss when said dental floss is being pulled out of said container;
   e) means in the chamber of said container for agitating said baking soda while said roughened dental floss is being pulled out of said container so that said baking soda can adhere to said roughened dental floss; and
   f) a cutter on said container for removing a piece of the roughened dental floss with particles of said baking soda adhered thereupon so it can be utilized in conjunction with hydrogen peroxide when used in areas between the teeth for the treatment of gingivitis.

2. An improved dental floss dispenser as recited in claim 1, wherein said roughening means includes:
   a) an expansion spring affixed at its lower end to the bottom of the chamber of said container; and
   b) a piece of perforated sandpaper affixed to the top end of said expansion spring so that said sandpaper will always make contact with said dental floss when said dental floss is being pulled out of said container.

3. An improved dental floss dispenser as recited in claim 2, wherein said agitating means includes a plurality of small balls in the chamber of said container so that when said container is vigorously shaken said small balls will agitate said baking soda to adhere to said roughened dental floss.

4. An improved dental floss dispenser as recited in claim 3, wherein said agitating means further includes:
   a) said shaft of said roll of dental floss being rotatably supported off center from its axis in the chamber of said container so that when said roll of dental floss rotates it will wobble back and forth to agitate said baking soda to adhere to said roughened dental floss; and
   b) a pair of spoons affixed transversely in opposite directions onto opposite sides of said shaft so that when said roll of dental floss rotates, said spoons will turn to also agitate said baking soda to adhere to said roughened dental floss.

* * * * *